| United States Patent [19] | [11] Patent Number: 5,312,448 |
|---|---|
| Högnelid et al. | [45] Date of Patent: May 17, 1994 |

[54] MEDICAL APPLIANCE FOR STIMULATING TISSUE CONTRACTIONS

[75] Inventors: Kurt Högnelid; Hans Strandberg, both of Sundybyberg; Nils Holmström, Järfälla, all of Sweden

[73] Assignee: Siemens Aktiengesellschaft, Munich, Fed. Rep. of Germany

[21] Appl. No.: 838,307

[22] PCT Filed: Sep. 7, 1990

[86] PCT No.: PCT/EP90/01516
§ 371 Date: Apr. 9, 1992
§ 102(e) Date: Apr. 9, 1992

[87] PCT Pub. No.: WO91/03272
PCT Pub. Date: Mar. 21, 1991

[30] Foreign Application Priority Data

Sep. 7, 1989 [EP] European Pat. Off. ........ 89116557.3

[51] Int. Cl.5 ............................................. A61N 1/36
[52] U.S. Cl. .......................................... 607/13; 607/38
[58] Field of Search ..................... 607/13, 27, 37, 38

[56] References Cited

U.S. PATENT DOCUMENTS

| 4,532,931 | 8/1985 | Mills . | |
|---|---|---|---|
| 4,558,702 | 12/1985 | Barreras et al. | 128/419 PG |
| 4,579,119 | 4/1986 | Callaghan | 607/13 |
| 4,726,379 | 2/1988 | Altman et al. . | |
| 4,821,724 | 4/1989 | Whigham et al. | 607/13 |
| 4,858,610 | 8/1989 | Callaghan et al. . | |

FOREIGN PATENT DOCUMENTS

| 0308563 | 3/1989 | European Pat. Off. . |
|---|---|---|
| 2119255 | 11/1983 | United Kingdom . |

*Primary Examiner*—William E. Kamm
*Assistant Examiner*—Kennedy J. Schaetzle
*Attorney, Agent, or Firm*—Hill, Steadman & Simpson

[57] ABSTRACT

An appliance for electrically stimulating tissue contractions of a living organism has circuitry for applying a stimulation potential to the tissue region to be stimulated and for applying a reference potential circuitry for detecting to the body of the living organism, stimulated tissue contractions. Following stimulation the stimulated tissue contraction is measured by a bipolar electrode between two adjacent tissue regions, the stimulation potential applied being to at least one of these tissue regions for the purpose of stimulating a tissue contraction.

9 Claims, 5 Drawing Sheets

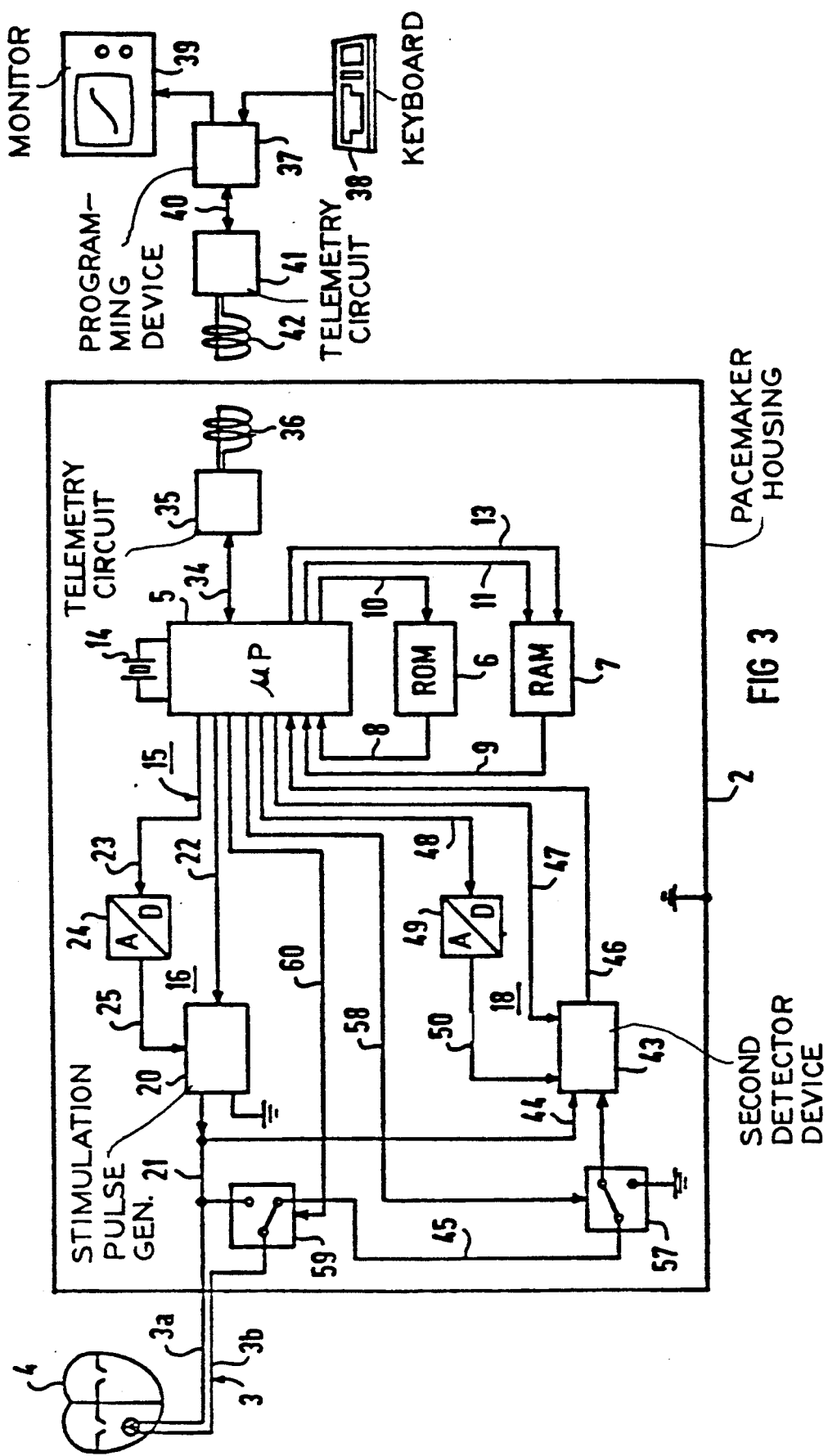

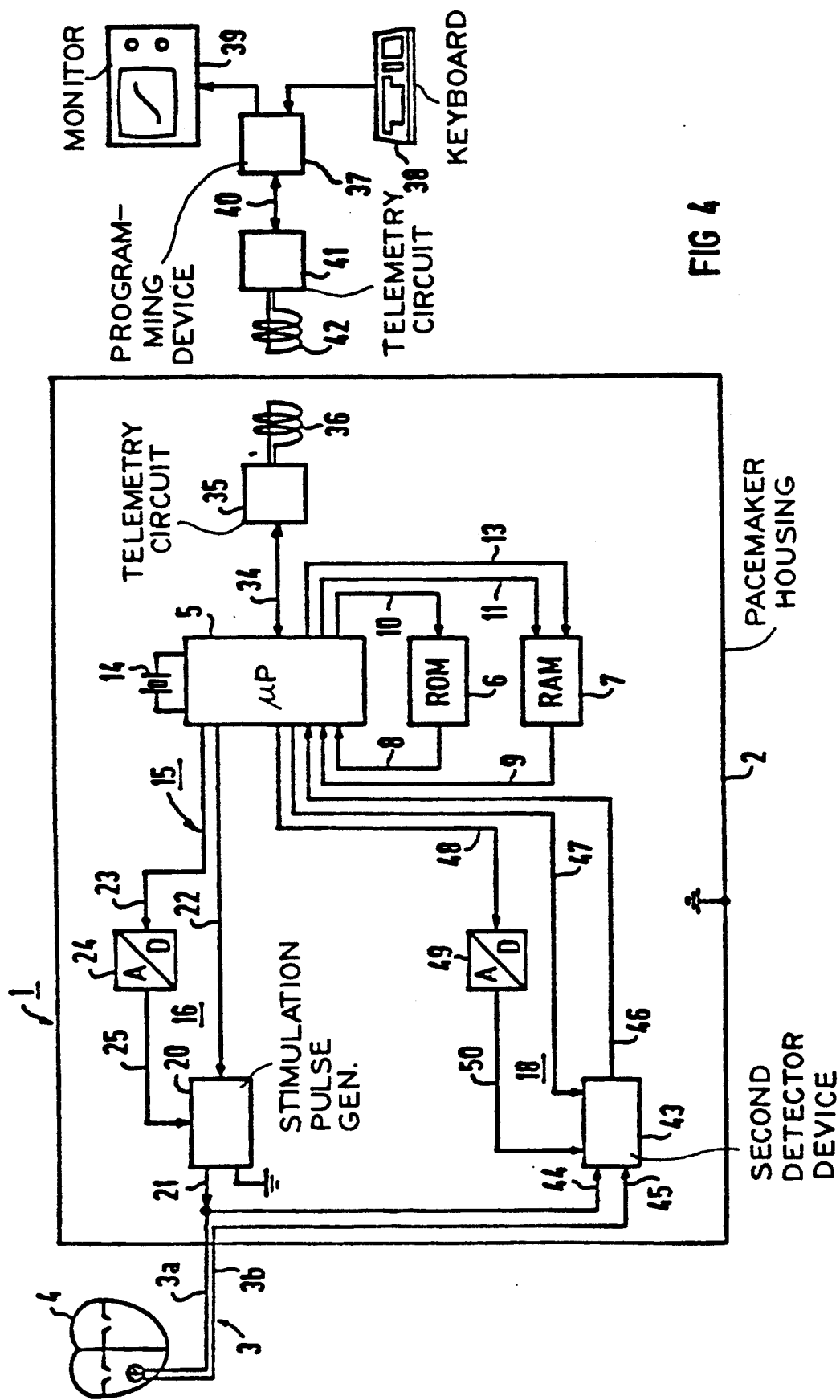

MEDICAL APPLIANCE FOR STIMULATING TISSUE CONTRACTIONS

BACKGROUND OF THE INVENTION

1. Field of the Invention

The present invention relates to a medical appliance which can be implanted in the body of a living organism, having means for electrically stimulating tissue contractions and a means for detecting stimulated tissue contractions.

2. Description of the Prior Art

A medical appliance in the form of a cardiac pacemaker is disclosed in European Application 0 236 562 having a terminal which carries the stimulation potential and a terminal which carries a reference potential. The means for detecting stimulated tissue contracts has two terminals and forms therefore a signal corresponding to the potential difference between the two terminals. The pacemaker has means for applying the reference potential to the body of the living organism, and a bipolar electrode which has two contact parts which can be brought into contact with the tissue to be stimulated stimulating a tissue contraction the terminal of the means for stimulation which carries the stimulation potential is connected to at least one of the two contact parts of the electrode and the terminal of the means for stimulation which carries the reference potential is connected to the means for applying the reference potential, and following stimulation one of the terminals of the means for detecting stimulated tissue contractions is connected to one of the two contact parts of the electrode.

More specifically, the aforementioned known cardiac pacemaker has means for stimulating the cardiac tissue, connected on the output side via a terminal which carries the stimulation potential to a first contact part at the distal end of the electrode and via a terminal which carries a reference potential to the housing of the cardiac pacemaker. Corresponding means are connected on the input side to the reference potential, to a second, annular contact part of the bipolar electrode, on the other, in order to detect the reaction of the heart to the stimulation (stimulation response). Due to the fact that the first contact part, to which the stimulation potential is applied, and the second contact part, which detects the stimulation response, are preferably arranged at a distance from one other of at least 0.5 cm, there is a reduction in the superimposition of the detected stimulation response by means of the polarization phenomena produced around the first contact part during the preceding stimulation in the tissue region.

SUMMARY OF THE INVENTION

In accordance with the principles of the invention in a medical appliance of the type present therefor; following stimulation the other terminal of the means for detecting stimulated tissue contractions is connected to the other contact part of the electrode. This stimulated tissue contraction is thus detected in a bipolar fashion between the two contact parts of the electrode. Although it is known, inter alia from U.S. Pat. Nos. 4,532,931, 4,726,379 and French Patent No. 2,524,808, to detect tissue contractions in a bipolar fashion, the previously known examples concern the detection only of spontaneous and not of stimulated tissue contractions. Because in the appliance according to the invention the two contact parts are in contact with the tissue region to be stimulated, in the region of the two contact parts the tissue will have approximately the same electrical potential following stimulation due to the polarization associated therewith. Since the means for detecting stimulated tissue contractions forms a signal corresponding to the potential difference between its terminals, and following stimulation these terminals are each connected to one contact part, the polarization of the tissue cannot therefore lead to any appreciable output signal of the means for detecting stimulated tissue contractions, which means that overloading of the means for detecting stimulated tissue contractions is prevented. If a stimulation triggers a tissue contraction, since the change in potential of the tissue associated with the stimulated tissue contraction propagates at a finite speed, the change in potential occurs at one of the contact parts earlier than at the other, so that a potential difference occurs between the two contact parts and thus between the terminals of the means for detecting stimulated tissue contractions. And thus the terminals deliver a signal corresponding to the detection of a stimulated tissue contraction. The distance between the contact parts should, however, not be less than one millimeter, in order to ensure that the time difference with which the change in potential associated with a stimulated tissue contraction occurs at the contact parts is sufficiently large to enable detection. It therefore becomes clear that reliable detection of stimulated tissue contractions is possible in a technically simple, cost-effective and energy-saving way using the appliance according to the invention.

According to a preferred variant of the invention, it is provided for the purpose of stimulating a tissue contraction that the terminal of the means for stimulation which carries the stimulation potential is connected to only one contact part of the electrode, and the distance between the contact parts of the electrode is at most five millimeters. Although only one of the contact parts of the electrode is connected to the terminal which carries the stimulation potential, it is ensured by this measure that following stimulation the tissue region which is to be stimulated is polarized to approximately the same extent in the region of the two contact parts of the electrode, since the distance of the contact parts is at most five millimeters. Overloading of the means for detecting stimulated tissue contractions is thus prevented.

A further preferred embodiment of the invention provides that switching means are provided which for the purpose of stimulating a tissue contraction that connect the terminal of the means for stimulation which carries the stimulation potential to the two contact parts of the electrode. As a result, following stimulation exactly the same tissue polarization is present in the region of the two contact parts, since the stimulation energy is applied to the tissue region to be stimulated in the region of the two contact parts. The contact parts can thus also be at a distance from one another which is more than five millimeters. However, it must be ensured that the two contact parts are still in contact with the tissue region to be stimulated, in order to prevent tissue regions which should not be stimulated from also experiencing stimulation.

A reliable detection of the stimulated tissue contractions is achieved in an advantageous way when the means for detecting stimulated tissue contractions contain a bandpass filter having a downstream threshold detector. In this case, the transfer function of the bandpass filter is selected such that only those signal components which, with regard to their frequency or slope are typical of stimulated tissue contractions, can pass the bandpass filter. According to an advantageous development of the invention, means for detecting spontaneous tissue contractions are provided and connected to a control logic which activates the means for stimulation in each case when no spontaneous tissue contraction can be detected by the means for detecting spontaneous tissue contractions before the expiration of a defined time interval. Stimulations of tissue contractions do not appear and stimulations are actually required.

It is not absolutely necessary in this case for there to be separate means for detecting spontaneous tissue contractions, since according to a preferred variant of the invention the means for detecting spontaneous tissue contractions can be formed by the means for detecting stimulated tissue contractions. With means for setting different sensitivities of the means for detecting stimulated or spontaneous tissue contractions being additionally provided. In order to enable unipolar detection of spontaneous tissue contractions, it is expedient in this case if switching means are provided by which, for the purpose of detecting spontaneous tissue contractions, a terminal of the means for detecting stimulated tissue contractions can be connected to the means for applying the reference potential.

However, it is preferable that the means for detecting both stimulated and spontaneous tissue contractions are permanently connected on the input side to the two contact parts of the electrode. This means that no switching means are required, and that the detection both of the stimulated and of the spontaneous tissue contractions is performed in a bipolar fashion by the same means. In this way, it is also easier to detect and eliminate possible interference signals, because the detection of the stimulated and spontaneous tissue contractions is performed continuously by the same means. In this regard, a reliable detection is achieved when the means for electrically stimulating tissue contractions generate a negative stimulation potential with interval for detecting stimulated tissue contractions, and, following stimulation, the means for setting different detection sensitivities set a first threshold at the threshold detector, which monitors the bandpass-filtered, signal for overshooting of the first threshold. Further, a subsequent second time interval for detecting spontaneous tissue contractions, the means for setting different detection sensitivities set a second threshold at the threshold detector, which monitors the bandpass-filtered signal for undershooting of the second threshold. Advantageous use is made in this case of the circumstance that in the signal corresponding to the stimulated tissue contraction the positive signal edge, and in a natural tissue contraction the negative signal edge, is in each case the steepest, and thus the best suited for reliable detection.

DESCRIPTION OF THE DRAWINGS

In order to explain the invention, reference is made below to the figures of the drawing, wherein:

FIG. 3 shows a second, and FIG. 4 shows a third exemplary embodiment for the cardiac pacemaker.

DESCRIPTION OF THE PREFERRED EMBODIMENTS

Figure 1:
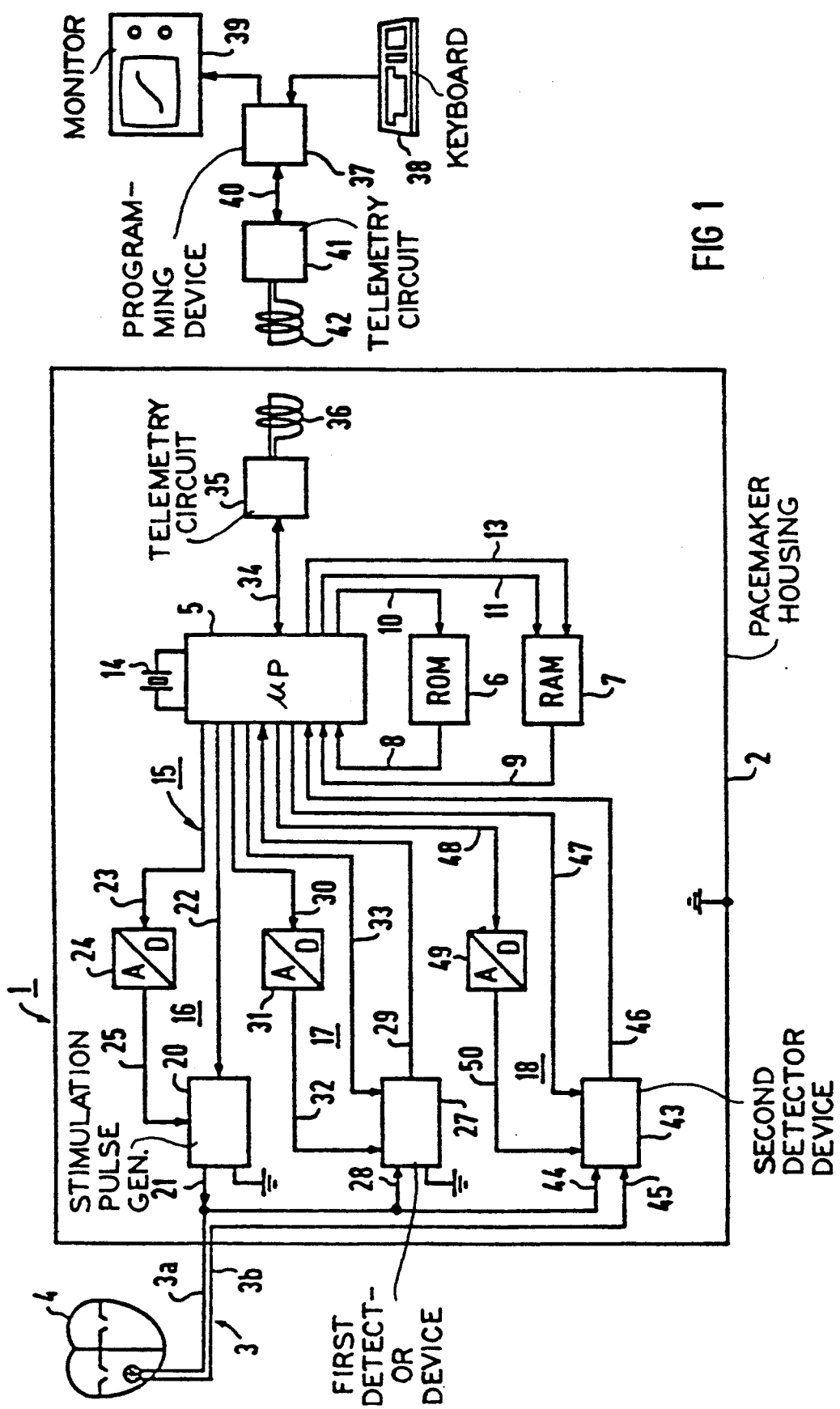
FIG. 1 shows a first exemplary embodiment of the appliance according to the invention embodied as a cardiac pacemaker.

In the exemplary embodiment shown in FIG. 1, an implantable cardiac pacemaker 1 has components accommodated in a hermetically tight, implantable housing 2, which is indicated schematically and is made of an electrically conductive material, for example titanium. A bipolar electrode 3 leads from the cardiac pacemaker operating in the VVI mode, to a schematically indicated heart 4 of a living organism, and is implanted there into a ventricle, preferably the right ventricle. The bipolar electrode 3 has two leads 3a and 3b.

Figure 2:
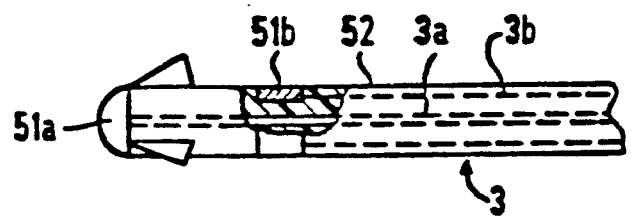
FIG. 2 shows an enlarged representation of the end of the electrode of the cardiac pacemaker provided for anchoring in the heart.

As may be seen from FIG. 2, the bipolar electrode 3 consists of a coaxial cable 52, whose inner conductor corresponds to the lead 3a and whose screen corresponds to the lead 3b. The leads 3a and 3b lead to two contact parts 51a and 51b which serve to contact the myocardial tissue electrically. The contact part 51a is constructed as a tip, while the contact part 51b is embodied as a ring. There is a distance of the order of magnitude of five millimeters between the two contact parts 51a, 51b.

The cardiac pacemaker 1 comprises, inter alia, a microprocessor 5 which is assigned a read-only memory (ROM) 6 and a random-access memory (RAM) 7 which are connected via respective data lines 8 and 9 and address lines 10 and 11 to the microprocessor 5. Moreover, a line 13 which serves to switch over the RAM 7 from write to read mode and vice versa leads from the microprocessor 5 to the RAM 7. A program by which all functions of the cardiac pacemaker 1 are controlled is stored in the ROM 6. Thus, when it is stated below that the microprocessor 5 executes a specific function, means this that the microprocessor 5 acts to execute the respective function by executing the program stored in the ROM 6, using data located in the RAM 7 and data added to it in another way, for example via an input circuit. When it is stated that the microprocessor 5 sets a specific value for a parameter, this means, if nothing else is specified, that stored data are in the RAM 7 corresponding to the specific value which the microprocessor 5 can access.

Connected to the microprocessor 5 is a quartz crystal 14, which serves to generate the clock signals required for operating the microprocessor 5, and furthermore represents the time reference for operating the cardiac pacemaker 1. The microprocessor 5 has an input/output circuit, which is designated as a whole by 15 and has a plurality of channels 16, 17 and 18.

The channel 16 serves, if required, to supply the heart 4 with electrical stimulation pulses for triggering stimulated myocardial contractions. The channel 16 therefore has a stimulation pulse generator 20 which has a terminal which is connected by an output line 21 with the lead 3a of the electrode 3 and carries the stimulation potential, as well as a terminal which carries a reference potential. The terminal which carries the reference potential is electrically conductively connected to the housing 2. This is illustrated by providing a ground symbol both for the terminal carrying the reference potential, for the stimulation pulse generator 20 and for the housing 2. Although there is a bipolar electrode 3, the stimulation is thus performed in a unipolar fashion, i.e. the stimulation potential is applied via the tip 51a of the electrode 3 to the myocardial tissue, and the reference potential outside the heart is applied to the tissue surrounding the housing 2 of the cardiac pacemaker 1. The stimulation pulse generator 20 can be activated to transmit a stimulation pulse via a line 22 which is connected to a corresponding output of the microprocessor 5. Digital data relating to the duration and the amplitude and thus the energy content of the stimulation pulses pass from the microprocessor 5 via a line 23 to a digital/analog interface 24 which feeds the stimulation pulse generator 20 via a control line 25 with analog control signals corresponding to the digital data. These control signals set the stimulation pulse generator 20 such that when required it generates stimulation pulses of a specific energy content and thus stimulates the heart 4 with a specific stimulation intensity.

The channel 17 has a first detector device 27, which serves exclusively to detect spontaneous myocardial contractions, i.e. natural heartbeats. The first detector device 27 has a signal input that is connected to the lead 3a of the electrode 3 via an input line 28, and a terminal which carries a reference potential. As is made clear by the ground symbol attached to the terminal carrying the reference potential, in this case the reference potential is the same reference potential which is also carried by the corresponding terminal of the stimulation pulse generator 20 and the housing 2. Although there is a bipolar electrode 3, in the exemplary embodiment according to FIG. 1 the detection of spontaneous myocardial contractions is thus also performed in a unipolar fashion by the first detector device 27. The signal corresponding to the electrical activity of the heart 4 is thus tapped by the tip 51a of the electrode 3, and the terminal, carrying the reference potential, of the first detector device 27 is at the potential of the tissue surrounding the housing 2 of the cardiac pacemaker 1. If the first detector device 27 detects a spontaneous myocardial contraction in the signal that is fed to it via the lead 3a of the electrode 3 and corresponds to the electrical activity of the heart 4, it supplies a signal via a line 29 to a corresponding input of the microprocessor 5. The first detector device 27 transmits this signal whenever an event having a slope and/or amplitude typical of a natural heartbeat occurs in the signal corresponding to the electrical activity of the heart. The microprocessor 5 is connected via a line 30 to a digital/analog interface 31 which passes analog signals to the first detector device 27 via a control line 32 corresponding to digital data from the microprocessor 5. The digital data or the corresponding analog signals serve to set the sensitivity of the second detector device 27, i.e., that slope and/or amplitude which an event in the signal corresponding to the electrical activity of the heart 4 must at least have in order to be detected as a natural heartbeat. Moreover, via a control line 33 the microprocessor 5 can feed a signal to the first detector device 27 which completely inhibits the latter, so that no signals indicating the detection of a natural heartbeat can pass to the microprocessor 5.

If the microprocessor 5 receives a signal via the line 29 a signal indicating the detection of a natural heartbeat by the first detector device 27, or if it activates the stimulation pulse generator 20 via the line 22 to transmit a stimulation pulse, the microprocessor 5 begins to operate as a counter and counts a number of clock pulses derived from the oscillation of the quartz 14 and corresponding to a base time interval. The base time interval determines that stimulation frequency at which the heart 4 is stimulated upon the non-appearance of natural heartbeats. If, during a base time interval, no signal that indicates the detection of a natural heartbeat passes via the channel 17, i.e. via the line 29, to the microprocessor 5, upon expiration of the base time interval the microprocessor 5 activates the stimulation pulse generator 20 via the line 22. Following the transmission of a stimulation pulse, the microprocessor 5 restarts counting a number of clock pulses which corresponds to the base time interval determining the stimulation frequency. If, by contrast, during the course of the base time interval the microprocessor 5 receives a signal indicating the detection of a natural heartbeat from the first detector device 27, it interrupts the above-described counting operation, if a further time interval (the so-called refractory period) has expired, and restarts the counting operation for determining the base time interval without the transmission of a stimulation pulse taking place. The detection of a natural heartbeat by the first detector device 27 after expiration of the refractory time thus inhibits the transmission of a stimulation pulse. The base time interval can be programmed, for example, to values of between 400 and 2000 ms. The refractory time is, in principle, shorter than the base time interval and lasts approximately between 250 and 450 ms (programmable). The refractory time is subdivided into an absolute refractory time and a relative refractory time subsequent thereto, the first detector device 27 being completely inhibited during the absolute refractory time.

The microprocessor 5 is connected via a line 34 to a telemetry circuit 35 to which a transmit/receive coil 36 is connected. The cardiac pacemaker 1 is thus capable of interchanging data by means of an external programming device 37 to which a keyboard 38 and a monitor 39 are connected, since the programming device 37 is connected via a line 40 to a second telemetry circuit 41 to which also has a transmit/receive coil 42 connected thereto. For the purpose of data interchange between the cardiac pacemaker 1 and the programming device 37, the transmit/receive coil 42 of the telemetry circuit 41 belonging to the programming device 37 is positioned on the surface of the body of the living organism in which the cardiac pacemaker 1 is implanted in such a way that it is inductively coupled to the transmit/receive coil 36 of the cardiac pacemaker 1. It is then possible for the data located in the ROM 6 and the RAM 7 to be fed for checking purposes to the programming device 27. Furthermore, it is possible to feed modified or additional data from the programming device 37 to the RAM 7 of the cardiac pacemaker 1 modified or additional data which influence or modify the operational performance of the cardiac pacemaker 1, that is, its interaction with the heart 4 to be stimulated. This process is conventionally designated as programming.

The channel 18 of the input/output circuit of the microprocessor 5 serves to make data available thereto which allow it on the basis of the program stored in the ROM 6 to set the stimulation intensity, i.e., the energy content of the stimulation pulses generated by the stimulation pulse generator 20, in such a way that a stimulation pulse also actually triggers a myocardial contraction, i.e., a stimulated heartbeat. For this purpose, the channel 18 contains a second detector device 43 which is provided exclusively for detecting stimulated myocardial contractions. The second detector device 43 has two terminals, of which one is connected via the line 44 to the lead 3a of the electrode 3 and thus to the tip 51a, and the other is connected via a line 45 to the lead 3b of the electrode 3 and thus to the ring 51b. By contrast with the already described first detector device 27, the second detector device 43 thus detects myocardial contractions which occur as a result of a stimulation pulse transmitted by the stimulation pulse generator 20. If the second detector device 43 detects a stimulated myocardial contraction, a corresponding signal passes via a line 46 from the output of the second detector device 43 to a corresponding input of the microprocessor 5. The microprocessor 5 is capable of inhibiting the input or output of the second detector device 43 via a control line 47 by a corresponding signal. The sensitivity of the second detector device 43 can be set by the microprocessor 5 in a way to be described in more detail by using the microprocessor 5 to feed digital data via a line ..48 to a digital/analog interface 49, which converts this data into a corresponding analog signal which is fed to the second detector device 43 via a control line 50.

Differing from the first detector device 27, whose output is released by the microprocessor 5 only after expiration of the absolute refractory time, in the case of the second detector device 43 it must be possible for detections to take place immediately after a stimulation, in order to enable stimulated myocardial contractions to be detected at all. The microprocessor 5 thus enables the second detector device 43 a few milliseconds after the transmission of a stimulation pulse for a short time interval, for example 100 ms, for the purpose of detecting stimulated myocardial contractions. However, it is important in this case that the detection of a stimulated myocardial contraction by the second detector device 43 cannot inhibit the transmission of a stimulation pulse by the stimulation pulse generator 20. This can take place only through the detection of a natural heartbeat by the first detector device 27 under the described preconditions.

Represented in FIG. 3 is a second exemplary embodiment for the cardiac pacemaker according to the invention, which differs in only a few points from that previously described, with the same elements in each embodiment being designated with the same reference symbols. The cardiac pacemaker according to FIG. 3 differs from that previously described firstly in omission of the channel 17 with the detector device 27. Consequently, the detector device 43 of the channel 18 serves not only to detect stimulated myocardial contractions, but also to detect spontaneous myocardial contractions. The microprocessor 5 therefore enables the input or output of the detector device 43 via the line 47 not only in the manner previously described following the transmission of a stimulation pulse, but moreover during each base time interval following the absolute refractory time, which is necessary in order to enable the detection of spontaneous myocardial contractions by the detector device 43. In this case, provision can be made for the microprocessor 5 to set, via the digital-/analog interface 49, different sensitivities of the detector device 43 for detecting stimulated or spontaneous myocardial contractions, As may be seen from FIG. 3, an electronic changeover switch 57 is located in the line 45 leading from the lead 3b connected (to the ring 51b of the electrode 3) to the detector device 43, which can be operated by the microprocessor 5 via a control line 58. In this case, the changeover switch 57 assumes, for detecting stimulated myocardial contractions, the switching position which is represented in FIG. 3 and in which the inputs of the detector device 43 are connected in the manner described with reference to FIG. 1 to the tip 51a or the ring 51b of the electrode 3. In order to detect spontaneous myocardial contractions, the microprocessor 5 moves the changeover switch 57 into its switching position that is not represented, in which the line 45 is connected to the reference potential and thus to the housing 2 of the cardiac pacemaker 1; the detection of spontaneous myocardial contractions thus takes place in a unipolar fashion.

A further difference is that the cardiac pacemaker according to FIG. 3 contains a further electronic changeover switch 59 which is operated by the microprocessor 5 via the control line 60. If the electronic changeover switch 59 assumes its switching position shown in FIG. 3, the lead 3b of the electrode 3 is connected to the line 45, as is necessary for detecting stimulated and spontaneous myocardial contractions. However, in order to transmit a stimulation pulse the microprocessor 5 operates the changeover switch 59 in such a way that the latter assumes its switching position which is not shown in FIG. 3 and in which the lead 3b of the electrode 3 is connected to the line 21 leading from the terminal, carrying the stimulation potential, of the stimulation pulse generator 20 to the lead 3a of the electrode 3. It is important in this case that the microprocessor 5 changes the switching position of the changeover switch 59 only for the duration of the stimulation pulse in the manner described. It thus becomes clear that the myocardial tissue is fed a stimulation pulse via both the tip 51a and the ring 51b of the electrode. Consequently, after the transmission of a stimulation pulse the myocardial tissue has the same polarization in each case both in the region of the tip 51a and in the region of the ring 51b of the electrode 3. Consequently, the distance between the tip 51a and the ring 51b of the electrode 3 can also be larger than five millimeters, without the risk of overloading the detector device 43. If the distance is less than five millimeters, the further changeover switch 59 can also be eliminated, just as the further changeover switch 59 in the exemplary embodiment according to FIG. 1 can be provided when the distance there between the contact parts 51a and 51b is greater than five millimeters.

Represented in FIG. 4 is a third exemplary embodiment of the cardiac pacemaker according to the invention, in which, as in the exemplary embodiment according to FIG. 3, the detector device 43 serves to detect both spontaneous and stimulated myocardial contractions. However, in a departure from the previously described exemplary embodiment the detector device 43 is permanently connected with its input-side terminals to the contact parts 51a and 51b of the electrode 3, so that the detection both of the spontaneous and of the stimulated myocardial contractions takes place in a bipolar fashion. After each stimulation pulse, the detector device 43 is activated for a prescribed time interval in order to detect a possible stimulated myocardial contraction, and subsequently after expiration of the refractory time in order to detect natural heartbeats. In this case, the microprocessor 5 can set different sensitivities of the detector device for detecting stimulated or spontaneous myocardial contractions via the digital/analog interface 49.

Figure 5:
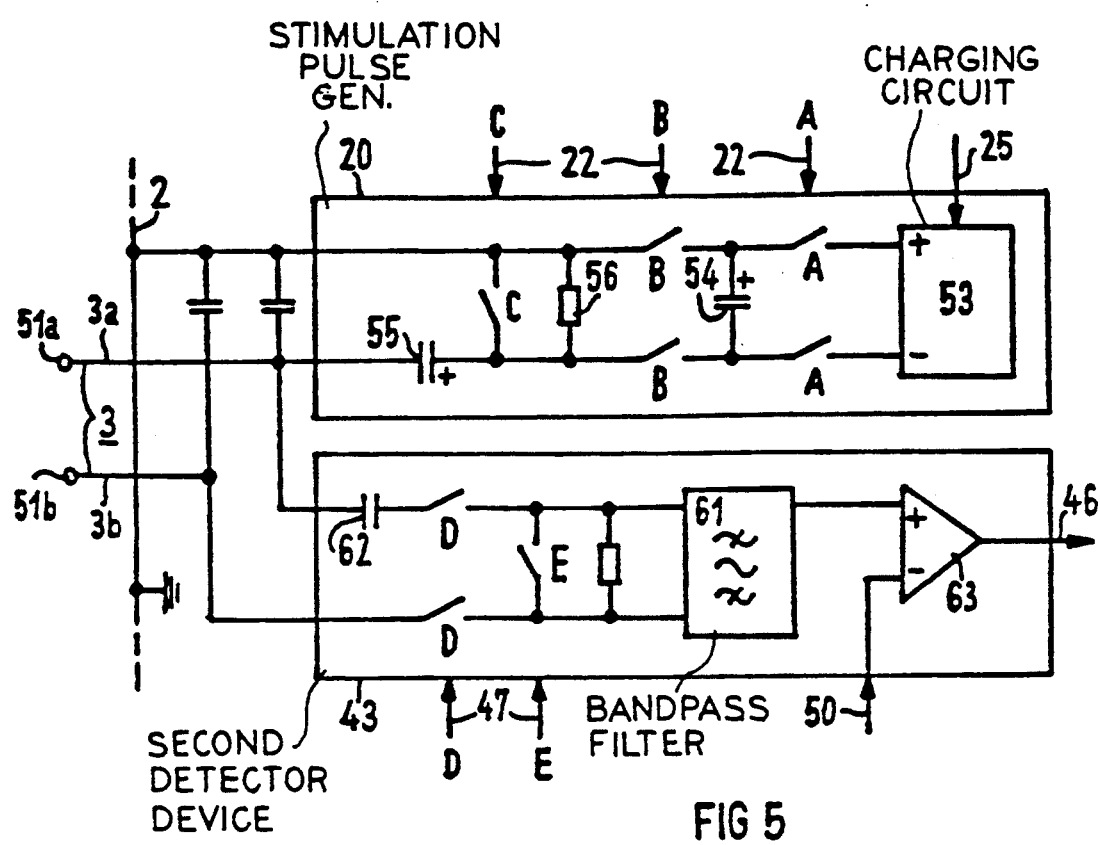
FIG. 5 shows a block diagram of the stimulation pulse generator and of the detector device for detecting stimulated myocardial contractions.

Represented in more detail in FIG. 5 are the stimulation pulse generator 20 and the detector device 43 in accordance with the configuration according to FIG. 4, which are specified in the different exemplary embodiments. The stimulation pulse generator 20 contains a battery-powered charging circuit 53 by which a charging capacitor 54, which is connected via a first pair of switches A to the output of the charging circuit 53, is charged to a voltage value predetermined by the microprocessor 5 via the digital/analog interface 24. The charging capacitor 54 is connected via a second pair of switches B at its terminal which carries a positive reference potential to the housing 2 of the cardiac pacemaker 1. The capacitor 54 is connected at its terminal which carries the negative stimulation potential via an output capacitor 55 to the contact part 51a on the tip of the electrode 3. Furthermore, a switch C with a high-resistance parallel resistor 56 is provided, which connects the contact part 51a via the output capacitor 55 to the cardiac pacemaker housing 2. On the input side, the detector device 43 has a bandpass filter 61 which is connected via a third pair of switches D and an input capacitor 62 to the two contact parts 51a and 51b of the electrode 3. The input of the bandpass filter 61 can be shortcircuited by a further switch E. Just like the switch C and the pairs of switches A, B and D, the further switch E is driven via the control lines 22 and 50 assigned thereto by the microprocessor 5. Apart from its filter function, the bandpass filter 61 can also perform signal amplification. The transfer function of the bandpass filter 61 is selected to pass only those signal components which with regard to their frequency or slope are typical of stimulated myocardial contractions. The output signal of the bandpass filter 61 passes to the noninverting input (+) of a comparator 63 which compares its amplitude with a threshold signal which is fed to its inverting input (−) via the control line 50. The threshold signal is the output signal of the digital/ analog interface 49. If the amplitude of the output signal of the bandpass filter 61 overshoots or undershoots the level of the threshold signal, the output signal of the comparator 63 jumps from its one extreme value to its other extreme value.

Figure 6:
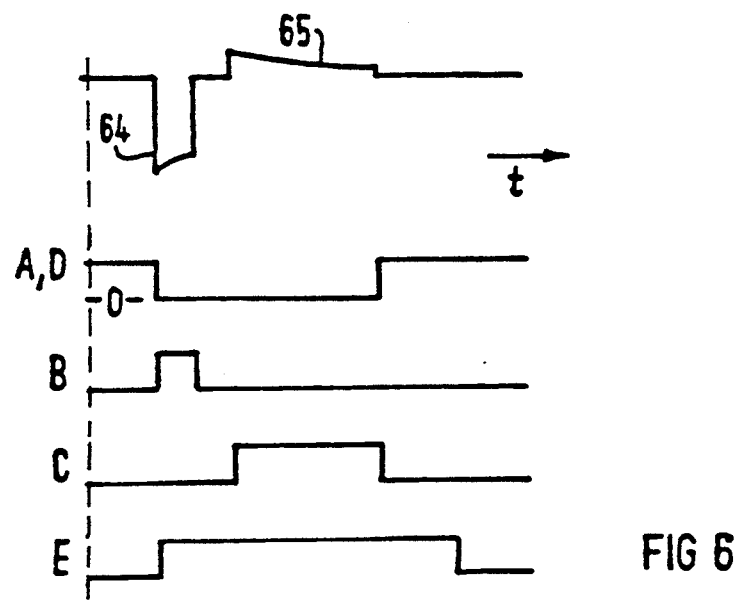
FIG. 6 shows a timing diagram with the stimulation pulse generated by the stimulation pulse generator and control signals for the circuit elements represented in FIG. 5.

FIG. 6 shows in a timing diagram an example of the negative stimulation pulse 64, generated by the stimulation pulse generator 20, with subsequent rapid discharge pulse 65, and the control signals that are transmitted by the microprocessor 5 to the pairs of switches A, B and D and to the switches C and E (designated in FIG. 6) for the purpose of controlling the stimulation pulse generator 20 and the detector device 43. In this case, a signal state departing from zero signifies that the assigned switch is closed. As long as the pair of switches A is closed, the charging capacitor 54 is charged to the output voltage generated by the charging circuit 53. In order to generate the negative stimulation pulse 64, the switch B is closed for the duration of approximately 1 ms while the pair of switches A is open. After a following short pause, the switch C is closed for approximately 4 ms, as a result of which the output capacitor 55 is rapidly discharged. Throughout the duration of the stimulation pulse complex 64 and 65, the input of the bandpass filter 61 is decoupled by the pair of switches D from the contact parts 51a and 51b of the electrode 3 and, in addition, shortcircuited is for a brief time longer via the further switch E.

Figure 7A:
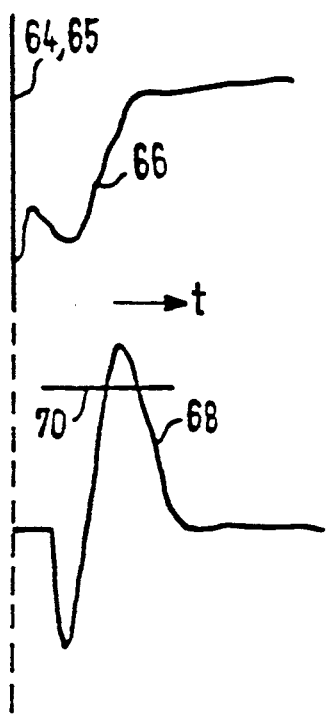
FIG. 7a shows characteristics of stimulated myocardial contractions upstream and downstream of bandpass filtering.
Figure 7B:
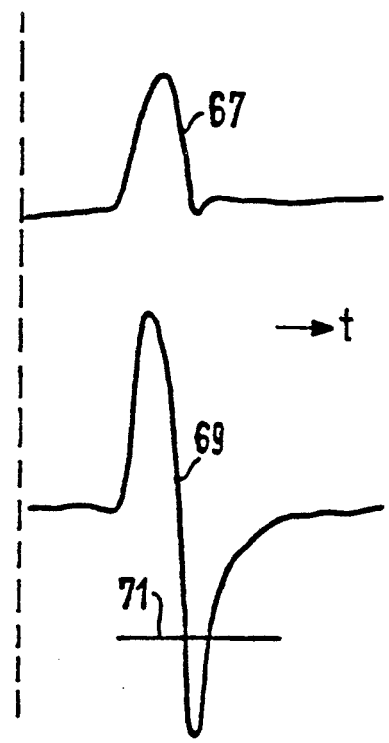
FIG. 7b shows characteristics of spontaneous myocardial contractions upstream and downstream of bandpass filtering.

For the purpose of explaining the detection of myocardial contractions by the detector device 43, FIG. 7 at the top represents the characteristic of a stimulated myocardial contraction 66 measured between the contact parts 51a and 51b, measured in a bipolar fashion, and the characteristic of a spontaneous, natural myocardial contraction 67. Below this are represented the corresponding respectively signal characteristics 68 and 69, after filtering via the bandpass filter 61. As may be seen from FIG. 7, the signal characteristic 66 of the stimulated myocardial contraction has a rapid positive edge of approximately 50 ms after the stimulation, which enables a reliable identification of the signal characteristic 66 as a response of the heart to a stimulation. The manner of the identification is that the threshold comparator 63 monitors the bandpass-filtered signal 68 for overshooting of a first positive threshold 70. The delay of the positive signal edge with respect to the stimulation pulse 64 means that, at the instant of the occurrence of the signal edge the polarization phenomena produced by the stimulation in the cardiac tissue have already decayed in large part. Furthermore, the influence of the polarization phenomena on the measured signal is reduced because of the short distance between the two contact parts 51a and 51b in the region of the polarized tissue, so that no appreciable signal induced by polarization occurs between the two contact parts 51a and 51b. Finally, the bandpass filter 63 has a blocking effect on the relatively slowly decaying polarization phenomena. In the signal characteristic 69 of a natural heartbeat, the negative signal edge is the most rapid and thus best suited for identifying the signal characteristic 69 by using the threshold comparator 63 to monitor the bandpass-filtered signal 69 for undershooting of a second, negative threshold 71.

The abovementioned automatic setting of the energy content of the stimulation pulses generated by the stimulation pulse generator 20 is performed in all three described exemplary embodiments in such a way that on each occasion after the transmission of a stimulation pulse the microprocessor 5 tests whether a signal indicating the detection of a stimulated myocardial contraction is being supplied from the output of the detector device 43 via the line 46. If this is not the case, the microprocessor 5 increases the energy content of the next stimulation pulse by feeding digital data to the digital/analog interface 24, which converts this data into an analog signal which sets the stimulation pulse generator 20 so that it transmits a stimulation pulse an energy content that is higher by a defined step with respect to the energy content previously transmitted. This takes place until a setting is found for the energy content of the stimulation pulses at which the detector device 43 detects a stimulated myocardial contraction after each stimulation pulse. In this case, the microprocessor 5 sets the stimulation pulse generator 20 via the digital/analog interface 24 so that the energy content of the generated stimulation pulses corresponds to the sum of a minimum energy content at which, after the transmission of a stimulation pulse, the detector device 43 still just detects a stimulated myocardial contraction, (plus a safety margin, for example 50% of the minimum energy content). In this case, the minimum energy content corresponds to the so-called threshold stimulation which the energy content of a stimulation pulse must at least reach in order to be able to trigger a stimulated myocardial contraction. For the purpose of determining the minimum energy content, the microprocessor 5 from time to time reduces the energy content of the stimulation pulses starting from a value at which, after each stimulation pulse of a sequence of stimulation pulses, the detector device 43 detects a stimulated myocardial contraction. This is done gradually in steps until no further stimulated myocardial contraction can be detected by the detector device 43, at least after individual stimulation pulses. Starting from this energy content of the stimulation pulses, the microprocessor 5 once again increases their energy content gradually in steps, just so far until after each stimulation pulse the detector device 43 once again detects a stimulated myocardial contraction. The value thus found represents the minimum energy content of the stimulation pulses, or the threshold stimulation of stimulation.

The described setting of the energy content of the stimulation pulses achieves, guarantees the safety of the patient, since the stimulation is always performed by stimulation pulses whose energy content is located by a safety margin above the minimum energy content. At the same time, it is ensured that the energy requirement of the appliance owing to the transmission of the stimulation pulses is not higher than necessary, since their energy content is always orientated to the required minimum energy content.

Although modifications and changes may be suggested by those skilled in the art, it is the intention of the inventors to embody within the patent warranted hereon all changes and modifications as reasonably and properly come within the scope of their contribution to the art.

We claim:

1. A medical appliance adapted for in vivo implantation in an organism comprising:
    means for electrically stimulating tissue contractions in said organism having a terminal carrying a stimulation potential and a terminal carrying a reference potential;
    means for detecting stimulated tissue contractions having an input side with two terminals, said means for detecting forming a signal corresponding to the potential difference between said two terminals;
    means for applying said reference potential to said organism;
    a bipolar electrode having two contact parts adapted for in vivo contact with tissue to be stimulated; and
    means, for the purpose of stimulating a tissue contraction, for connecting said terminal carrying said stimulation potential to at least one of said two contact parts of said bipolar electrode and for connecting said terminal carrying said reference potential to said means for applying said reference potential, and following stimulation, for connecting one of said two terminals of said means for detecting to one of said two contact parts of said electrode and for connecting the other of said two terminals of said means for detecting to the other of said two contact parts of said electrode.

2. An appliance as claimed in claim 1 wherein said means for connecting, for the purpose of stimulating a tissue contraction, connects said terminal carrying said stimulation potential to only one contact part of said bipolar electrode, and wherein said two contact parts of said bipolar electrodes are spaced from each other at a distance not greater than 5 mm.

3. An appliance as claimed in claim 1 wherein said means for connecting is a multi-pole electronic switching arrangement.

4. An appliance as claimed in claim 1 wherein said means for detecting includes a bandpass filter followed, in a direction of signal propagation, by a threshold detector.

5. An appliance as claimed in claim 1 further comprising:
    means for detecting spontaneous tissue contractions; and
    control logic means for activating said means for stimulating tissue contractions whenever no spontaneous tissue contraction is detected by said means for detecting spontaneous tissue contractions before the expiration of a defined time interval.

6. An appliance as claimed in claim 5 wherein said means for detecting spontaneous tissue contractions consists of said means for detecting stimulated tissue contractions and means for setting different sensitivities of said means for detecting stimulated tissue contractions.

7. An appliance as claimed in claim 6 further comprising switching means, for the purpose of detecting spontaneous tissue contractions, for connecting one of said two terminals of said means for detecting stimulated tissue contractions to said means for applying said reference potential.

8. An appliance as claimed in claim 6 wherein said means for detecting stimulated tissue contractions, forming a part of said means for detecting spontaneous tissue contractions, is permanently connected to said two contact parts of said bipolar electrode.

9. An appliance as claimed in claim 1 wherein said means for detecting stimulated tissue contractions includes a bandpass filter followed by a threshold detector in a direction of signal propagation, said means for detecting stimulated tissue contractions forming, in combination with a means for setting different sensitivities of said means for detecting stimulated tissue contractions, a means for detecting spontaneous tissue contractions, said appliance further comprising control logic means for activating said means for stimulating tissue contractions whenever no spontaneous tissue contraction is detected by said means for detecting spontaneous tissue contactions before the expiration of a defined time interval, said means for stimulating tissue contractions including means for generating a negative stimulation potential with respect to said reference potential, and wherein said means for setting different sensitivities includes means for setting, during a first time interval for detecting stimulated tissue contractions following stimulation, a first threshold of said threshold detector for monitoring said signal after filtering by said bandpass filter for overshooting said first threshold, and for setting, in a subsequent second time interval for detecting spontaneous tissue contractions, a second threshold of said threshold detector for monitoring said signal after filtering by said bandpass filter for undershooting said second threshold.

* * * * *